United States Patent
Inou et al.

(10) Patent No.: US 9,808,583 B2
(45) Date of Patent: Nov. 7, 2017

(54) PERCUTANEOUS MEDICATION DEVICE AND NEEDLE FORMATION USED FOR THE DEVICE

(75) Inventors: Akinori Inou, Yoshida-cho (JP); Akihiro Shinoda, Yoshida-cho (JP); Kouichi Otsuka, Yoshida-cho (JP)

(73) Assignee: Nanbu Plastics Co., Ltd., Shizuoka (JP)

( * ) Notice: Subject to any disclaimer, the term of this patent is extended or adjusted under 35 U.S.C. 154(b) by 81 days.

(21) Appl. No.: 13/817,039

(22) PCT Filed: Aug. 19, 2011

(86) PCT No.: PCT/JP2011/004640
§ 371 (c)(1),
(2), (4) Date: Mar. 28, 2013

(87) PCT Pub. No.: WO2012/026100
PCT Pub. Date: Mar. 1, 2012

(65) Prior Publication Data
US 2013/0184648 A1    Jul. 18, 2013

(30) Foreign Application Priority Data

Aug. 23, 2010 (JP) ................................. 2010-186653

(51) Int. Cl.
*A61M 5/32* (2006.01)
*A61M 5/34* (2006.01)
*A61M 5/00* (2006.01)

(52) U.S. Cl.
CPC ........ *A61M 5/3202* (2013.01); *A61M 5/3287* (2013.01); *A61M 5/343* (2013.01);
(Continued)

(58) Field of Classification Search
CPC .... A61M 5/3202; A61M 5/343; A61M 5/349; A61M 5/3287; A61M 5/002;
(Continued)

(56) References Cited

U.S. PATENT DOCUMENTS 3,158,155 A * 11/1964 Myerson ................. A61M 5/24
604/202
4,592,744 A *  6/1986 Jagger ................... A61M 5/002
600/576
(Continued)

FOREIGN PATENT DOCUMENTS

CN          1856333 A    11/2006
CN       101557848 A    10/2009
(Continued)

OTHER PUBLICATIONS

International Search Report, dated Nov. 22, 2011, for PCT/JP2011/004640, 2 pages.
(Continued)

*Primary Examiner* — Bhisma Mehta
*Assistant Examiner* — Jenna Zhang
(74) *Attorney, Agent, or Firm* — Seed IP Law Group LLP

(57) ABSTRACT

A percutaneous medication device, comprising a syringe to be filled with medical liquid and a needle formation attached to a leading-end of the syringe is provided. The needle formation comprises a needle formation body, from the surface of which a needle projects and a cover portion covers a leading-end of the needle formation body. The needle is inserted into a through-hole formed at the leading-end of the needle formation body and fixed by a fixation member. The needle formation body is mated to the cover portion, a space is formed between an inner surface of the cover portion and the leading-end of the needle formation body, and the needle projects from the leading-end surface of the cover portion
(Continued)

through a needle insertion hole formed at the leading-end of the cover portion.

8 Claims, 4 Drawing Sheets

(52) U.S. Cl.
CPC ............. *A61M 5/349* (2013.01); *A61M 5/002* (2013.01); *A61M 5/3298* (2013.01)

(58) Field of Classification Search
CPC .... A61M 5/3298; A61M 5/3295; A61M 5/34; A61M 5/344; A61M 5/348; A61M 5/3293; A61M 5/346
USPC .................................. 604/110, 263, 192–198
See application file for complete search history.

(56) References Cited

U.S. PATENT DOCUMENTS

| | | | | |
|---|---|---|---|---|
| 5,466,226 A | * | 11/1995 | van den Haak | ... A61M 5/31511 604/192 |
| 5,968,021 A | * | 10/1999 | Ejlersen | ............. A61M 5/3213 206/365 |
| 6,391,003 B1 | * | 5/2002 | Lesch, Jr. | ............... A61M 5/30 604/110 |
| RE42,355 E | * | 5/2011 | Heiniger | ............... A61M 5/326 604/110 |
| 2005/0038392 A1 | * | 2/2005 | DeSalvo | ............. A61M 5/3243 604/198 |
| 2007/0149924 A1 | | 6/2007 | Marsh | |
| 2007/0191780 A1 | * | 8/2007 | Modi | .................... A61M 5/282 604/187 |
| 2010/0030152 A1 | | 2/2010 | Lee et al. | |
| 2010/0234811 A1 | * | 9/2010 | Schubert | ............... A61M 5/326 604/198 |
| 2010/0286618 A1 | * | 11/2010 | Choi | ....................... A61M 5/32 604/173 |

FOREIGN PATENT DOCUMENTS

| | | |
|---|---|---|
| JP | 2005087521 A | 4/2005 |
| JP | 2007502156 A | 2/2007 |
| JP | 2007054194 A | 3/2007 |
| JP | 2009511192 A | 3/2009 |
| JP | 2009-526575 A | 7/2009 |
| JP | 2010508058 A | 3/2010 |

OTHER PUBLICATIONS

Chinese Office Action, dated Mar. 2, 2015, for corresponding Chinese Application No. 201180040833.5, 5 pages, with partial translation.

* cited by examiner

PERCUTANEOUS MEDICATION DEVICE AND NEEDLE FORMATION USED FOR THE DEVICE

BACKGROUND

Technical Field

The present invention relates to a percutaneous medication device for percutaneously administering a medical liquid and a needle formation used for the percutaneous medication device.

Description of the Related Art

Conventionally, a syringe is used for administrating a medical liquid or medicine (hereinafter, referred to as medical liquid) which cannot be perorally administered. However, the level of stress to a body in a method for using a syringe is large and is accompanied by pain. Although a method of percutaneous administration of medicine with a patch has been used, this method takes a long time to express a medical effect and usable medicine is limited.

In order to solve these problems, Japanese Laid-Open Publication No. 2005-87521 (Patent Literature 1), Japanese National Phase PCT Laid-Open Publication No. 2010-508058 (Patent Literature 2) and Japanese Laid-Open Publication No. 2007-54194 (Patent Literature 3) proposed a percutaneous medication device using a small diameter needle to reduce a pain due to centesis of a needle at injection.

In these percutaneous medication devices, a needle is fixed by use of an adhesive and the like so that the needle projects by a predetermined dimension from the leading-end surface of the device. However, as shown in FIG. 1 of Patent Literature 3, since a hardened component of the adhesive remains on the leading-end surface of the device, a projection dimension of the needle from the surface of the hardened component of the adhesive is affected by the size of the hardened component of the adhesive. For this reason, there is a defect that, if an application amount of an adhesive varies, a projection dimension is not consistent.

CITATION LIST

Patent Literature

PTL 1
Japanese Laid-Open Publication No. 2005-87521
PTL 2
Japanese National Phase PCT Laid-Open Publication No. 2010-508058
PTL 3
Japanese Laid-Open Publication No. 2007-54194

SUMMARY OF INVENTION

Technical Problem

The present invention has been made for solving the above-described problem; an objective is to provide a percutaneous medication device which can stabilize a projection dimension of a needle from the body surface and a needle used for the device.

BRIEF SUMMARY

Solution to Problem

In order to solve the above-described problem, the present invention is characterized by the following terms.

A percutaneous medication device, comprising: a syringe which is filled with medical liquid and a needle formation attached to a leading-end of the syringe, wherein the needle formation comprises a needle formation body, in which a needle projects from a leading-end surface and a cover portion covering a leading-end of the needle formation body;

the needle is inserted into a through-hole formed at the leading-end of the needle formation body; and the needle is fixed to the needle formation body by a fixation means;

the needle formation body is mated to the cover portion and a space is formed between an inner surface of the cover portion and the leading-end surface of the needle formation body, and the needle projects from a leading-end surface of the cover portion through a needle insertion hole formed at the leading-end of the cover portion.

The percutaneous medication device according to the present invention, wherein the cover portion has a resilient piece contacting an outer surface of the needle formation body, a engaging portion is formed on the outer surface of the needle formation body, and an engaged portion which can be engaged to the engaging portion on the resilient piece.

The percutaneous medication device according to the present invention, wherein the fixation member is an adhesive, and the hardened component is arranged within the space.

The percutaneous medication device according to the present invention further comprises a needle holder, wherein the needle formation is arranged in unrotatable condition within the needle holder and the needle formation is housed in an aseptic condition within the needle holder by a removable seal disposed in the needle holder.

The percutaneous medication device according to an embodiment of the present invention, wherein the needle formation can be attached to the leading-end of the syringe by a Luer lock structure.

The percutaneous medication device according to the present invention, wherein a step portion is formed on an inner surface of the cover portion and a leading-end surface of the needle formation body abuts to the step portion to form the space between the inner surface of the cover portion and the leading-end surface of the needle formation body.

A needle formation attached to a leading-end of a syringe, wherein the needle formation comprises a needle formation body, in which a needle projects from a leading-end surface and a cover portion covering a leading-end of the needle formation body, the needle is inserted into a through-hole formed at the leading-end of the needle formation body, and the needle is fixed to the needle formation body by a fixation means, the needle formation body is mated to the cover portion, and a space is formed between an inner surface of the cover portion and the leading-end surface of the needle formation body, and the needle projects from a leading-end surface of the cover portion through a needle insertion hole formed at the leading-end of the cover portion.

The needle formation according to the present invention, wherein the fixation member is adhesive and a hardened component of the adhesive is disposed within the space.

The needle formation according to the present invention, wherein a step portion is formed on an inner surface of the cover portion, and a leading-end surface of the needle formation body abuts to the step portion to form the space between the inner surface of the cover portion and the leading-end surface of the needle formation body.

Advantageous Effects of Invention

A needle formation comprises a needle formation body in which a needle projects from a leading-end surface and a cover portion covering a leading-end of the needle formation body, the needle is inserted into a through-hole formed at the leading-end of the needle formation body, and the needle is fixed to the needle formation body by a fixation means; the needle formation body is mated to the cover portion, a space is formed between an inner surface of the cover portion and the leading-end surface of the needle formation body, and the needle projects from a leading-end surface of the cover portion through a needle insertion hole formed at the leading-end of the cover portion. Therefore, the fixation member for fixing the needle to the needle formation body is disposed within the space formed between the inner surface of the cover portion and the leading-end surface of the needle formation body. For this reason, a variation of an application amount (the size of a hardened component) of the fixation member does not affect the projection dimension of the needle from a surface of the cover portion.

The needle formation comprises a needle formation body and a cover portion covering a leading-end of the needle formation body; the cover portion has a resilient piece contacting an outer surface of the needle formation body, an engaging portion formed on the outer surface of the needle formation body, and an engaged portion which can be engaged to the engaging portion on the resilient piece; thereby the needle formation can be easily configured simply by mating the needle formation body to the cover portion.

The needle formation is arranged in a needle holder, the needle formation is isolated in an aseptic condition by a removable seal member, the needle formation is arranged in unrotatable condition within the needle holder, and the needle formation can be attached to the leading-end of the syringe by a Luer lock structure; thereby the needle formation can be housed in an aseptic condition within the needle holder and, in addition, by attaching the needle formation to the leading-end of the syringe by the Luer lock structure to rotate the needle formation, the needle formation can be taken out from the needle holder.

As described above, the medical liquid injection device of the present invention can support narrower a needle to reduce pain while puncturing the skin and, in addition, a projection dimension of the needle from the surface of the needle body can be constant.

DETAILED DESCRIPTION

Figure 1:
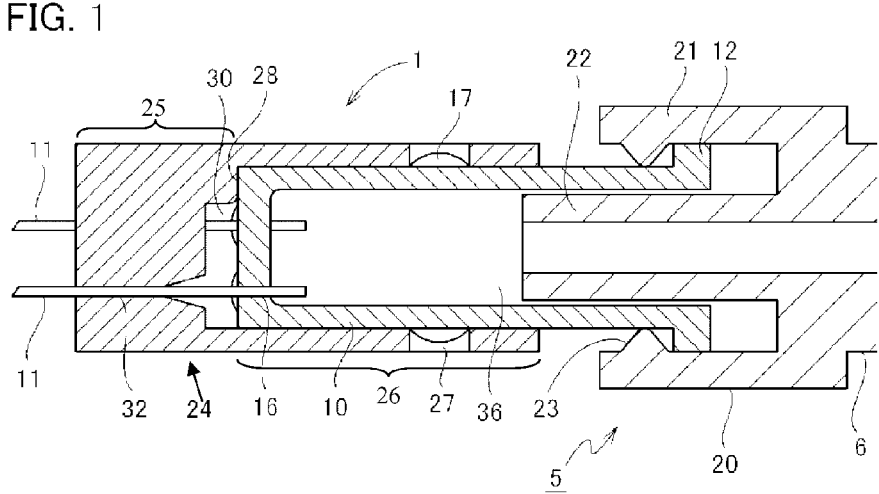
FIG. 1 is a cross-sectional view with a needle formation attached to a leading-end of a syringe.
Figure 2:
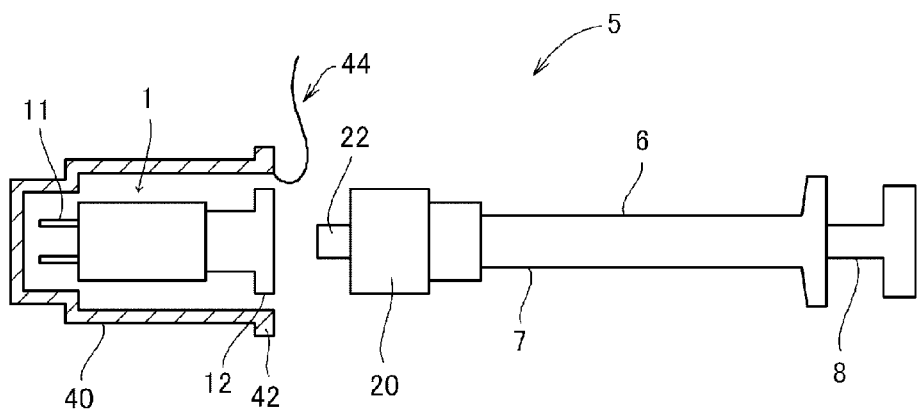
FIG. 2 is a cross sectional view of the syringe and the needle formation with the needle formation arranged within a needle holder.

In the following, embodiments of the present invention will be explained in detail by referring to the Figures.

As shown in FIG. 1 to FIG. 4, the percutaneous medication device 5 of the present invention comprises a syringe 6 to be filled with a medical liquid, a needle formation 1 attached to a leading-end of the syringe 6, and a needle holder 40 housing the needle formation 1 in an aseptic condition.

The syringe 6 comprises: a syringe body 7, a plunger 8 which is inserted into the syringe body 7, and a Luer lock portion 20 formed at a leading-end of the syringe body 7. The Luer lock portion 20 comprises an outer cylinder 21 and an inner cylinder 22, wherein a screw 23 is formed on an inner surface of the outer cylinder 21.

Figure 7:
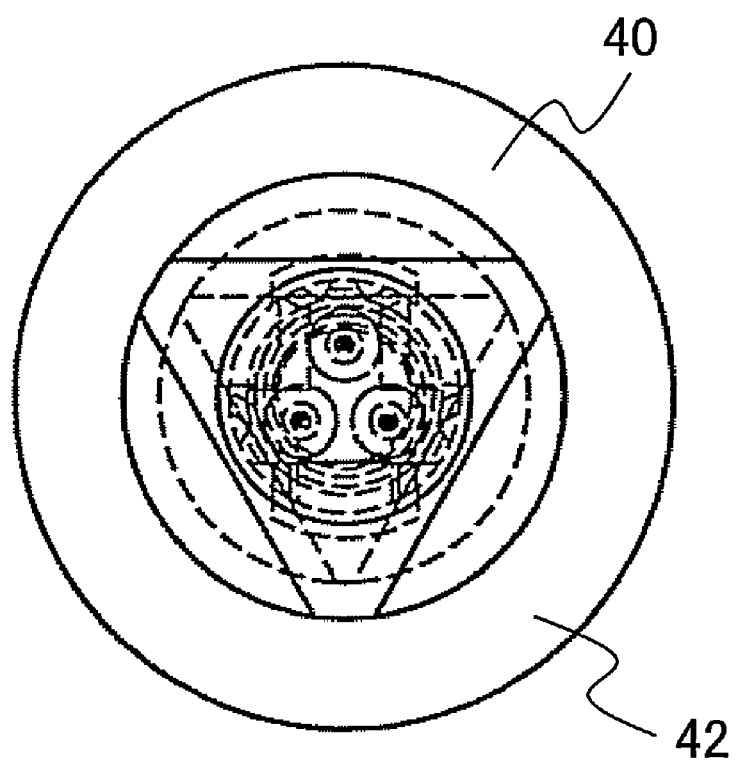
FIG. 7 is a perspective view with the needle formation arranged in the needle holder.

The needle formation 1 comprises a needle formation body 10 in which a needle 11 projects from the leading-end surface thereof and a cover portion 24 covering the leading-end of the needle formation body 10. The needle formation body 10 is formed in generally cylindrical shape, one end of which is open, and a flange 12 which can engage the Luer lock portion 20 is formed on a base end of the needle formation body 10. At the leading-end of the needle formation body 10, a through-hole 16 is formed to pass the needle 11. As shown in FIG. 7, in the present embodiment, three through-holes 16 are formed; however, the through-holes formed may be two or, equal to or more than four.

The needle 11 is inserted into the through-hole 16 and the needle 11 is fixed to the needle formation body 10 by a fixation member 18 such as adhesive. The fixation method of the needle 11 is not limited to methods which use adhesive; for example, methods such as a fusion (a heat seal, an ultrasonic fusion, a high frequency fusion) and the like may be used.

Figure 4:
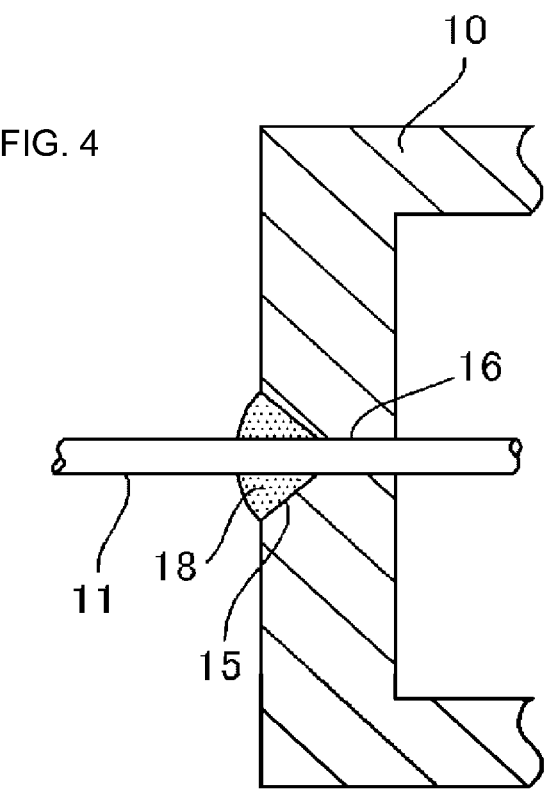
FIG. 4 is an enlarged cross-sectional view of the substantial part of the needle formation.

As shown in FIG. 4, a mortar-shaped recess 15 is formed on a surface of a leading-end of the needle formation body 10, in the periphery of the through-hole 16, and an adhesive 18 can be applied into the through-hole 16 through the recess 15.

On an outer surface of the needle formation body 10, a semi-circular protrusion is projected as an engaging portion 17.

The cover portion 24 comprises a head portion 25 and a plurality of resilient pieces 26 which are integrally extended to the needle formation body 10 side from the head portion 25. In the head portion 25, a needle insertion hole 32, through which the needle 11 can pass, is formed at the position of the needle 11. Three resilient pieces 26 are formed in the present embodiment; however, the resilient pieces 26 formed may be equal to or more than four.

In the resilient pieces 26, an engaging hole 27 is formed as an engaged portion at the position corresponding to an engaging portion (protrusion) 17 formed on an outer surface of the needle formation body 10.

In an inner surface of the head 25, a step portion 28 is formed. When the needle formation body 10 is inserted into an inside of the cover portion 24, and is mated, the leading-end surface of the needle formation body 10 abuts against the step portion 28 to form a space 30 between an inner surface of the leading-end of the cover portion 24 and a leading-end surface of the needle formation body 10.

At that time, the protrusion 17 of the needle formation body 10 engages with the engaging hole 27 formed on the resilient pieces 26 of the cover portion 24 in a snap fit.

Thus, when mating the needle formation body 10 with the cover portion 24, the needle 11 projects from the leading-end surface of the cover portion 24 through the needle insertion hole 32 formed at the leading-end of the cover portion 24 and the fixation member 18 does not protrude distally over the inner surface of the cover portion 24 (FIG. 1).

Figure 3:
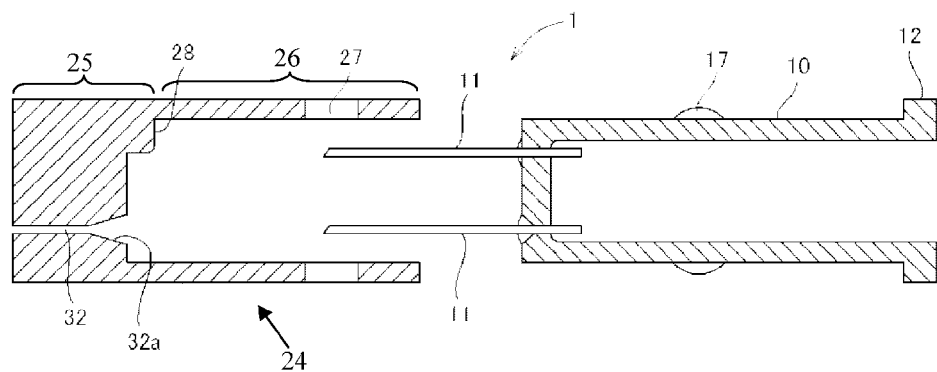
FIG. 3 is an exploded cross-sectional view of a needle formation body and a cover portion configuring the needle formation.

As shown in FIG. 3, the needle insertion hole 32 may be formed in a conical shape so that the inner diameter becomes greater nearer to the needle formation body 10. By forming a conical shaped portion 32a with taper at an open side of the needle insertion hole 32, the needle 11 which projects from the leading-end of the needle formation body 10 can be inserted into the insertion hole 32 easily and without a resin of the cover portion 24 adhering to a needle tip.

Examples of a constitution material for the needle 11 are, but are not limited to, a metallic material such as a stainless steel, an aluminum or aluminum alloy, a titanium or titanium alloy, and the like. The projection dimension of the needle 11 projecting from a surface of the needle formation 1, it is preferably equal to or less than 3 mm; more preferably, within the range of 0.5 mm to 2.0 mm, and further preferably, within the range of 0.5 mm to 1.5 mm. The maximum outer diameter of the needle 11 is preferably within the range of 0.1 mm to 0.6 mm, and, further preferably, within the range of 0.2 mm to 0.6 mm. The tip of the needle 11 is shaped as obliquely-cut tubular member.

The needle formation 1 can be manufactured by injection molding and the like with a thermoplastic resin such as polycarbonate, polypropylene, ABS resin, polystyrene and the like as a material.

Figure 5:
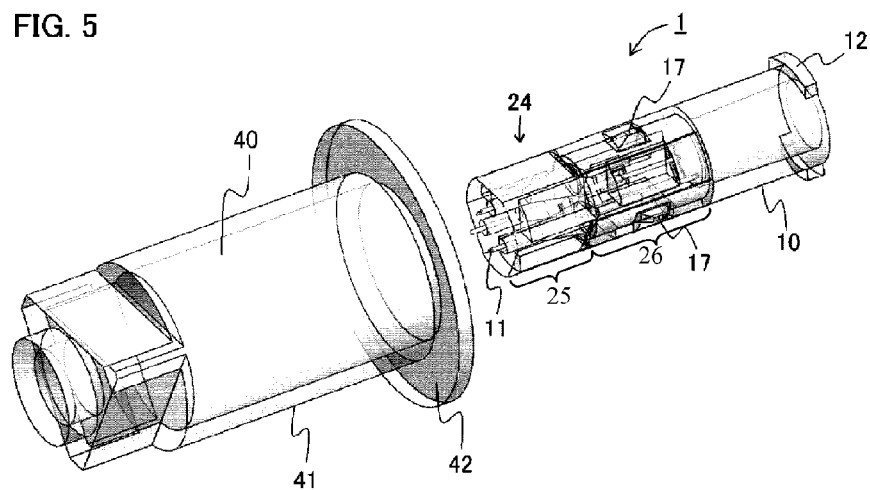
FIG. 5 is a cross-sectional view with the needle formation housed within the needle holder.
Figure 6:
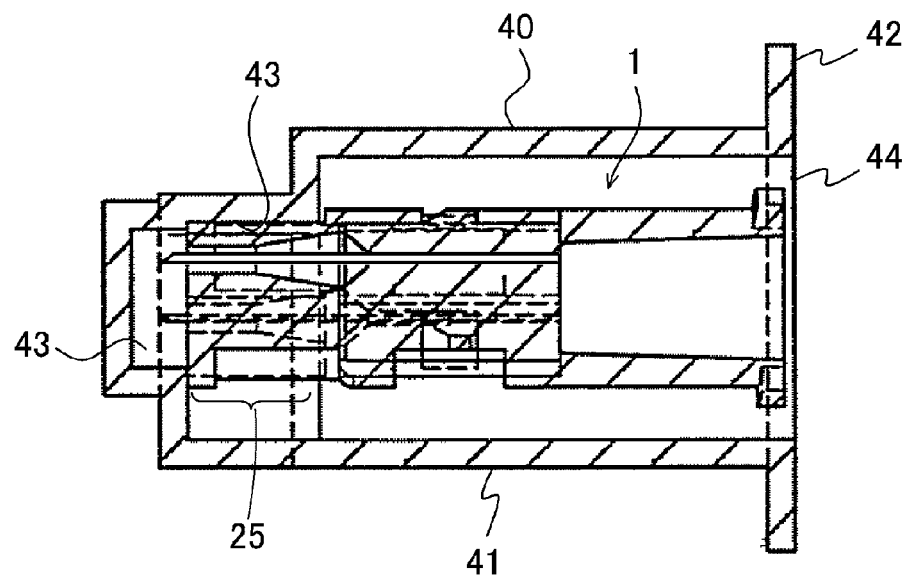
FIG. 6 is a cross-sectional view from a leading-end with the needle formation shown in FIG. 5 housed within the needle holder.

The above-described needle holder 40 comprises, as shown in FIG. 5 to FIG. 7, a holder body 41 formed in generally cylindrical shape, one end of which is open, and a flange 42 formed at the open end side of the holder body 41. A recess 43 with triangular-shaped cross-section is formed on an inner surface of the leading-end side of the holder body 41. This recess 43 is formed so that the shape of the recess 43 coincides with the shape of the leading-end of the cover portion 24 of the needle formation 1. That is, the outer shape of the head portion 25 of the cover portion 24 is generally triangular, and when, inserting the head portion 25 of the cover portion 24 into the recess 43 of the holder body 41, the needle formation 1 cannot be rotated relative to the holder body 41.

A seal member 44 which can close the open end of the holder body 41 is adhered to the flange 42 of the holder body 41. The seal member 44 seals the open end of the holder body 41 to isolate the needle formation 1 housed in the needle holder 40 in an aseptic condition. The open end can be opened by removing the seal member 44 from the flange 42 using a finger or the like.

Next, the operation method of the percutaneous medication device 5 of the present invention will be explained.

Since the needle formation 1 is stored in the needle holder 40 in an aseptic condition, the seal member 44 of the needle holder 40 is removed from the flange to outwardly expose the needle formation 1.

Next, holding the needle holder 40 by a finger or the like, the Luer lock portion 20 formed at a leading-end of the syringe 6 is engaged to the flange 12 of the needle formation 1 to rotate the syringe 6. Since the needle formation 1 cannot rotate relative to the needle holder 40, the Luer lock portion 20 of the syringe 6 and the flange 12 of the needle formation 1 are engaged. With this state, when the syringe 6 is pulled out from the needle holder 40, the needle formation 1 is attached to the leading-end of the syringe 6 (FIG. 1).

Then, according to the general method, by pressing the plunger 8 of the syringe 6, a medical liquid in the syringe 6 enters the space portion 36 of the needle formation 1; furthermore, the medical liquid is pushed out from the tip of the needle 11 through the needle 11 of the needle formation 1.

The medial liquid used in the medical liquid injection device 1 is, typically, a solution containing medical agent, gel or suspension. Usable medical agent is not substantially limited other than medical agent which is not suitable to be used for percutaneous administration.

The followings are examples of main medical agents: Hyaluronic acid, collagen, botox, antimicrobial agents, virucide, vaccine, antitumor agents, immunosuppressant, steroid, antiphlogistic, antirheumatic, antiarthritic, antihistamines, antiallergic agents, diabetes drugs, hormonal agents, bone/calcium metabolic agents, vitamin, hematic preparation, hematinic, antithrombotic agents, antihyperlipidemia agents, antiarrhythmic agent, vasodilator, prostaglandin, calcium antagonist, ACE inhibitor, beta blocker, depressor, diuretic, xanthine derivative, beta agonist, antiasthma agents, antitussive, expectorant, anticholinergic agents, stegnotic, stomachic digestant, antiulcerative, cathartic, narcoleptic, sedative, antipyretic, cold medicine, antiepileptic agents, antipsychotic agents, antidepressant, antianxiety agents, analeptic, parasympathomimetic agents, sympathetic agents, antiemetic, analeptic, antiparkinsonian agents, muscle relaxant, antispasmodic, anesthetic, antipruritic agents, antimigraine headache agents, diagnostic agents, oligonucleotide, gene agents and the like.

Here, medicines are preferably protein, peptide, polysaccharide, oligonucleotide, DNA and the like which do not express the effect or diminish in a peroral administration, specifically, high molecular weight drug such as insulin, growth hormone, interferon, calcitonin, and the like.

The cross-sectional shape of the needle formation 1 need not be circular, but may be square or an ellipsoidal shape. Furthermore, the shape of the recess 43 formed inside the needle holder 40 and the outer shape of the head portion 25 of the cover portion 24 are not limited to a triangular shape; instead, the shapes may be square, ellipsoidal, or the like. Spline may be formed on an inner surface of a wall of the needle holder 40 to be engaged with a convex portion formed on an outer surface of the needle formation 1. The convex portion may be formed on an outer surface of the needle formation body 10. A taper may be disposed on the recess 43 of the needle holder 40 to configure the needle holder such that the leading-end of the needle formation 1 is easily inserted into the recess 43.

In this embodiment, at a position of the leading-end surface of the needle formation 1, three needles 11 are formed at the positions of an equal distance from a center and with a separation angle of 120 degrees each other. However, this embodiment does not limit positions and number of the needles 11.

REFERENCE SIGNS LIST 1 a needle formation
5 a percutaneous medication device
6 a syringe
10 a needle formation body
11 needle 18 a fixation member
24 a cover portion
30 a space
40 a needle holder

The invention claimed is:

1. A percutaneous medication device, comprising:
a syringe to be filled with medical fluid, the syringe including a syringe body with a leading-end through which the medical fluid is dispensed and a movable plunger provided within the syringe body for dispensing the medical fluid; and
a needle formation attached to the leading-end of the syringe body,
wherein the needle formation comprises a needle formation body having a leading-end surface, a needle projecting from the leading-end surface of the needle formation body, a cover portion covering a leading-end of the needle formation body, and a fixation member configured to fix the needle to the needle formation body,
wherein the needle is inserted into a through-hole formed at the leading-end of the needle formation body and the needle is fixed to the needle formation body by the fixation member,
wherein the cover portion comprises a monolithically formed structure that includes (i) a leading-end wall located at a leading-end of the cover portion and having a leading-end wall surface that faces the leading-end surface of the needle formation body, (ii) one or more sidewalls projecting from an outer perimeter of the leading-end wall in a longitudinal direction, and (iii) a step portion projecting beyond the leading-end wall surface of the leading-end wall in the same longitudinal direction as the one or more sidewalls,
wherein when the leading-end surface of the needle formation body abuts to the step portion to form a space between the leading-end surface of the leading-end wall of the cover portion and the leading-end surface of the needle formation body, at least a portion of the needle projects out of the cover portion through a needle insertion hole formed in the leading-end wall of the cover portion, at least a portion of the fixation member is disposed on the leading-end surface of the needle formation body and is exposed to the space formed between the leading-end surface of the leading-end wall of the cover portion and the leading-end surface of the needle formation body, and the fixation member does not protrude beyond the leading-end surface of the leading-end wall of the cover portion, and
wherein the needle formation, which comprises the needle formation body, the needle, the cover portion, and the fixation member, is removably attachable to the leading-end of the syringe body as a single assembled unit to enable attachment of the needle formation to the leading-end of the syringe body prior to dispensing the medical fluid.

2. The percutaneous medication device according to claim 1, wherein each of the one or more sidewalls comprise a resilient piece contacting an outer surface of the needle formation body,
wherein a first engaging portion is formed in the resilient piece, and a second engaging portion is formed on the outer surface of the needle formation body, and
wherein the first engaging portion is releasably engaged with the second engaging portion.

3. The percutaneous medication device according to claim 1, wherein the fixation member is an adhesive.

4. The percutaneous medication device according to claim 1, further comprising a needle holder, wherein the needle formation is arranged in an unrotatable condition within the needle holder, and the needle formation is housed in an aseptic condition within the needle holder by a removable seal disposed in the needle holder.

5. The percutaneous medication device according to claim 1, wherein the needle formation is attached to the leading-end of the syringe body by a Luer lock structure.

6. The percutaneous medication device according to claim 1, wherein a mortar-shaped recess is formed on the leading-end surface of the needle formation body in the periphery of the through-hole, and the fixation member is applied into the through-hole through the mortar-shaped recess.

7. A needle formation attachable to of a syringe, the syringe including a syringe body with a leading-end through which medical fluid is dispensed and a movable plunger provided within the syringe body for dispensing the medical fluid, wherein the needle formation comprises a needle formation body having a leading-end surface, a needle projecting from the leading-end surface of the needle formation body, a cover portion covering a leading-end of the needle formation body, and a fixation member configured to fix the needle to the needle formation body,
wherein the needle is inserted into a through-hole formed at the leading-end of the needle formation body, and the needle is fixed to the needle formation body by the fixation member,
wherein the cover portion comprises a monolithically formed structure that includes (i) a leading-end wall located at a leading-end of the cover portion and having a leading-end wall surface that faces the leading-end surface of the needle formation body, (ii) one or more sidewalls projecting from an outer perimeter of the leading-end wall in a longitudinal direction, and (iii) a step portion projecting beyond the leading-end wall surface of the leading-end wall in the same longitudinal direction as the one or more sidewalls,
wherein when the leading-end surface of the needle formation body abuts to the step portion to form a space between the leading-end surface of the leading-end wall of the cover portion and the leading-end surface of the needle formation body, at least a portion of the needle projects out of the cover portion through a needle insertion hole formed in the leading-end wall of the cover portion, at least a portion of the fixation member is disposed on the leading-end surface of the needle formation body and is exposed to the space formed between the leading-end surface of the leading-end wall of the cover portion and the leading-end surface of the needle formation body, and the fixation member does not protrude beyond the leading-end surface of the leading-end wall of the cover portion, and
wherein the needle formation, which comprises the needle formation body, the needle, the cover portion, and the fixation member, is removably attachable to the leading-end of the syringe body as a single assembled unit to enable attachment of the needle formation to the leading-end of the syringe body prior to dispensing medical fluid.

8. The needle formation according to claim 7, wherein a mortar-shaped recess is formed on the leading-end surface of the needle formation body in the periphery of the through-hole, and the fixation member is applied into the through-hole through the mortar-shaped recess.

\* \* \* \* \*